US009763621B1

(12) United States Patent
Hafezi (10) Patent No.: US 9,763,621 B1
(45) Date of Patent: Sep. 19, 2017

(54) PREGNANCY BELT (71) Applicant: Marjan Hafezi, San Carlos, CA (US)

(72) Inventor: Marjan Hafezi, San Carlos, CA (US)

( * ) Notice: Subject to any disclaimer, the term of this patent is extended or adjusted under 35 U.S.C. 154(b) by 0 days.

(21) Appl. No.: 15/069,974

(22) Filed: Mar. 15, 2016

(51) Int. Cl.
| G08B 23/00 | (2006.01) |
| A61B 5/00 | (2006.01) |
| A41C 1/10 | (2006.01) |
| A61B 5/11 | (2006.01) |
| A61B 5/024 | (2006.01) |
| A41C 1/14 | (2006.01) |
| G08B 21/04 | (2006.01) |

(52) U.S. Cl.
CPC ............ *A61B 5/6831* (2013.01); *A41C 1/10* (2013.01); *A41C 1/14* (2013.01); *A61B 5/0026* (2013.01); *A61B 5/02411* (2013.01); *A61B 5/1116* (2013.01); *A61B 5/4362* (2013.01); *A61B 5/6823* (2013.01); *A61B 5/7405* (2013.01); *A61B 5/746* (2013.01); *A61B 5/7455* (2013.01); *G08B 21/0446* (2013.01)

(58) Field of Classification Search
None
See application file for complete search history.

(56) References Cited

U.S. PATENT DOCUMENTS

| 5,081,447 A | 1/1992 | Echols |
| 5,381,801 A | 1/1995 | McShane et al. |
| 5,913,834 A | 6/1999 | Francais |
| 5,935,749 A | 8/1999 | Kawata et al. |
| 7,817,035 B2 | 10/2010 | Hardacker et al. |
| 2004/0100376 A1 | 5/2004 | Lye et al. |
| 2007/0024457 A1 | 2/2007 | Long et al. |
| 2008/0100459 A1 | 5/2008 | Hoffman et al. |
| 2009/0045966 A1* | 2/2009 | Rocznik ............ A41D 13/1281 340/573.7 |
| 2010/0201526 A1* | 8/2010 | Hafezi ................ A61B 5/0002 340/573.7 |
| 2011/0132378 A1* | 6/2011 | Levendowski .......... A61B 5/11 128/848 |
| 2015/0289822 A1* | 10/2015 | Dugan ................. A61B 5/0077 600/301 |
| 2016/0310062 A1* | 10/2016 | Larson ................ A61B 5/4362 |
| 2016/0317091 A1* | 11/2016 | Olukoya .............. A61B 5/6831 |

\* cited by examiner

*Primary Examiner* — Brent Swarthout
(74) *Attorney, Agent, or Firm* — The Law Office of Herbert T. Patty (57) ABSTRACT

The present disclosure relates generally to the field of pregnancy devices. More specifically, the present disclosure relates to a wearable apparatus that alerts an expecting mother of unsafe lying or sleeping positions. An exemplary wearable apparatus consistent with the present disclosure comprises an adjustable belt member having an elongated axis of sufficient length to cover the girth of an expecting mother during the entire term of her pregnancy. Further, an attachment coupled to the wearable apparatus is present to secure the alarm belt to the expecting mother. In addition, sensors coupled to the wearable apparatus detect when the expecting mother is lying or sleeping in a supine position in which the sensors send signals to an external alarm. Furthermore, a power source may be coupled to the sensors to provide power thereto.

20 Claims, 7 Drawing Sheets

FIGURE 1

Supine

FIGURE 2

Right Lateral Recumbent

Left Lateral Recumbent

PREGNANCY BELT

FIELD

The present disclosure relates generally to the field of devices for pregnant women. More specifically, the present disclosure relates to a wearable apparatus that alerts an expecting mother of unsafe lying and sleeping positions.

BACKGROUND

Supine hypotensive syndrome is a medical condition caused when the inferior vena cava is compressed by the weight of a pregnant female's (expecting mother's) uterus, fetus, placenta, and amniotic fluids while lying in a supine position (lying on the back). Supine hypotensive syndrome can cause distress for the expecting mother's fetus which may lead to fetal hypoxia which in extreme cases results in a fetus' demise.

Fortunately, supine hypotensive syndrome can be easily prevented by monitoring the expecting mother's lying or sleeping position. Preferably, the expecting mother should lie and sleep in the left-lateral recumbent position.

The present disclosure provides a solution to prevent the cause of supine hypotensive syndrome as will be described in detail below.

SUMMARY OF THE PRESENT DISCLOSURE

The following summary is included in order to provide a basic understanding of some aspects and features of the present disclosure. This summary is not an extensive overview of the disclosure and as such it is not intended to particularly identify key or critical elements of the disclosure or to delineate the scope of the disclosure. Its sole purpose is to present some concepts of the disclosure in a simplified form as a prelude to the more detailed description that is presented below.

The present disclosure relates generally to the field of pregnancy devices. More specifically, the present disclosure relates to a wearable apparatus that alerts an expecting mother of unsafe lying or sleeping positions. An exemplary wearable apparatus consistent with the present disclosure comprises an adjustable belt member having an elongated axis of sufficient length to cover the girth of an expecting mother during the entire term of her pregnancy. Further, an attachment coupled to the wearable apparatus is present to secure the alarm belt to the expecting mother. In addition, sensors coupled to the wearable apparatus detect when the expecting mother is lying or sleeping in a supine position in which the sensors send signals to an external alarm. Furthermore, a power source may be coupled to the sensors to provide power thereto.

BRIEF DESCRIPTION OF THE DRAWINGS

To facilitate understanding, identical reference numerals have been used, where possible, to designate identical elements that are common to the drawings. The drawings are not to scale and the relative dimensions of various elements in the drawings are depicted schematically and not necessarily to scale. The techniques of the present disclosure may readily be understood by considering the following detailed description in conjunction with the accompanying drawings, in which.

DETAILED DESCRIPTION

A detailed description of some embodiments is provided below along with accompanying figures. The detailed description is provided in connection with such embodiments, but is not limited to any particular example. The scope is limited only by the claims and numerous alternatives, modifications, and equivalents are encompassed. Numerous specific details are set forth in the following description in order to provide a thorough understanding. These details are provided for the purpose of example and the described techniques may be practiced according to the claims without some or all of these specific details. For the purpose of clarity, technical material that is known in the technical fields related to some embodiments have not been described in detail to avoid unnecessarily obscuring the description.

The present disclosure relates generally to the field of pregnancy devices. More specifically, the present disclosure relates to a wearable apparatus that alerts an expecting mother of unsafe lying or sleeping positions. An exemplary wearable apparatus consistent with the present disclosure comprises an adjustable belt member having an elongated axis of sufficient length to cover the girth of an expecting mother during the entire term of her pregnancy. Further, an attachment coupled to the wearable apparatus is present to secure the alarm belt to the expecting mother. In addition, sensors coupled to the wearable apparatus detect when the expecting mother is lying or sleeping in a supine position in which the sensors send signals to an external alarm. Furthermore, a power source may be coupled to the sensors to provide power thereto.

Figure 1:
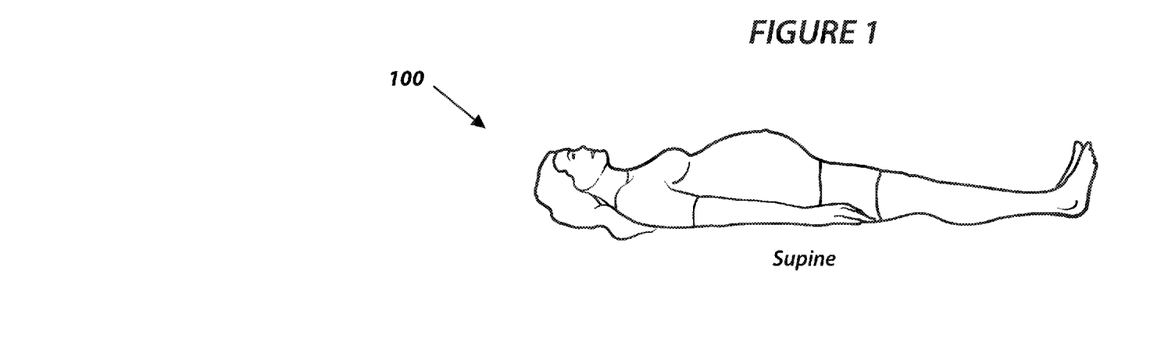
FIG. 1 is a schematic perspective view of an expecting mother lying in a supine position.

FIG. 1 is a schematic perspective view of an expecting mother lying in a supine position 100. Lying in the supine position can potentially cause supine hypotensive syndrome which may lead to symptoms of dizziness, sweating, nausea, hypotension, pallor, tachycardia, and other ailments. Fortunately, the effects of supine hypotensive syndrome can be relieved by changing the expecting mother's position while lying down.

Figure 2:
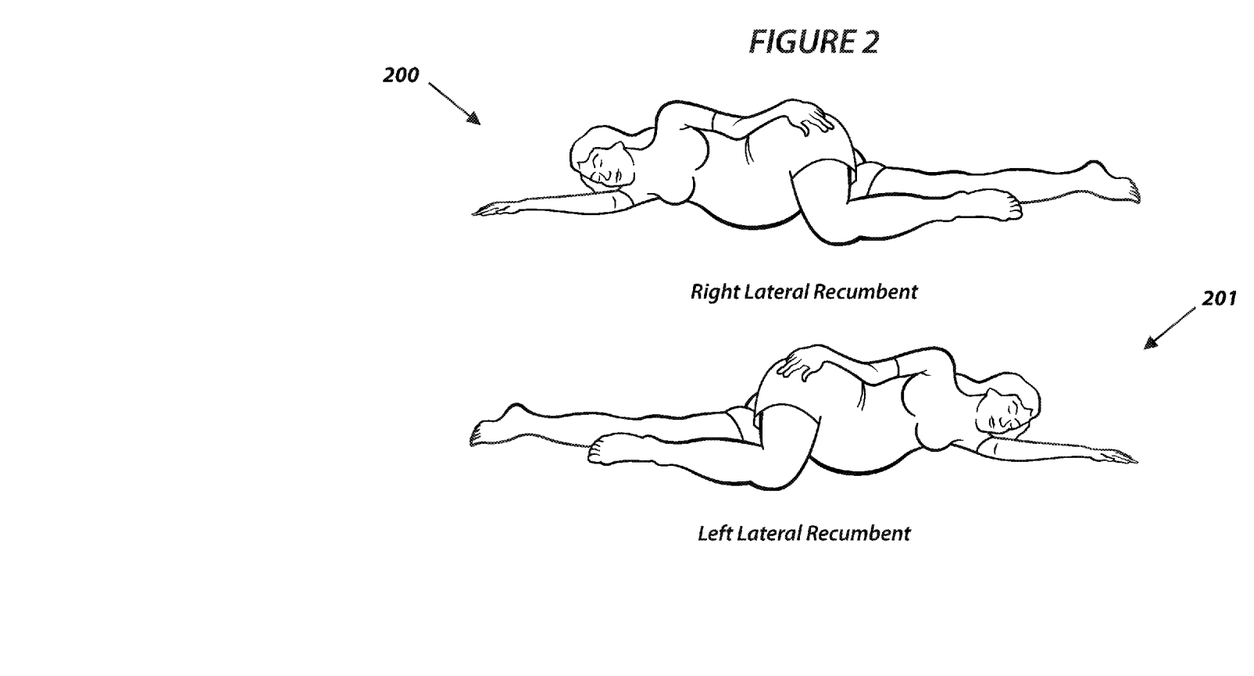
FIG. 2 is a schematic perspective view of the expecting mother lying in a right and left-lateral recumbent position.

FIG. 2 is a schematic perspective view of an expecting mother lying in a right lateral recumbent position 200 and a left-lateral recumbent position 201. Preferably, the expecting mother should lie in the left-lateral recumbent position 201 although lying in the right lateral recumbent position 200 may be sufficient to relieve symptoms of supine hypotensive syndrome.

Figure 3:
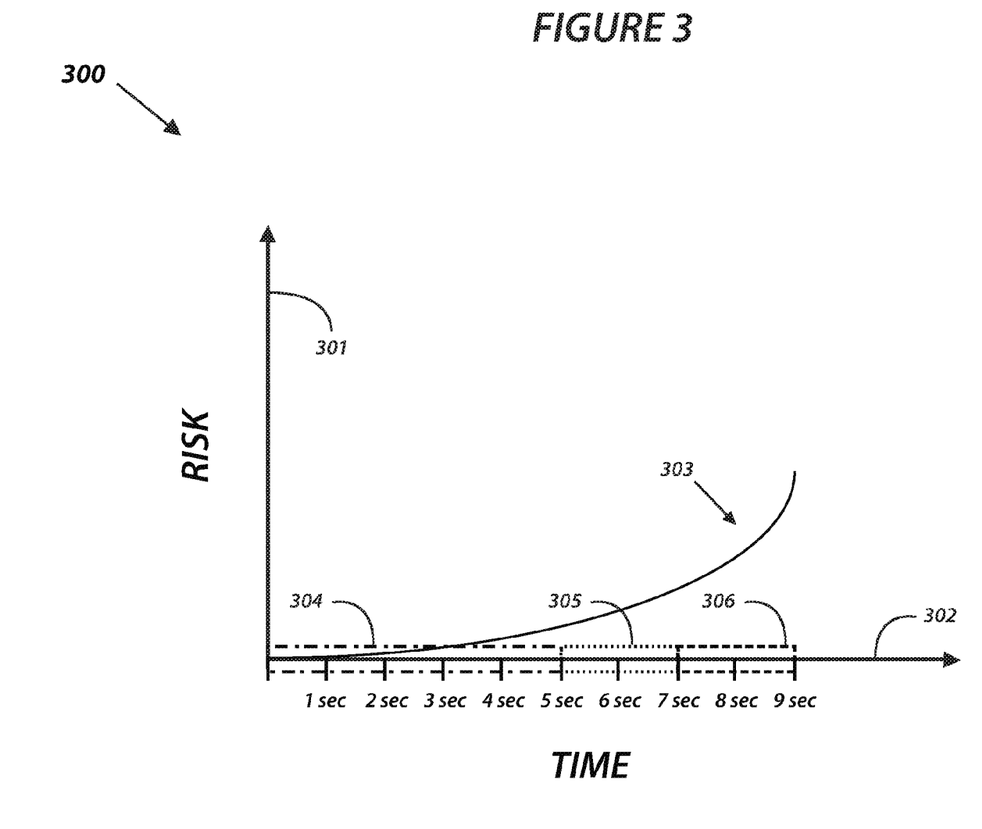
FIG. 3 is a graph displaying the risk of fetal hypoxia as a result of the expecting mother lying in a supine position.

FIG. 3 is a graph 300 displaying the risk of fetal hypoxia as a result of an expecting mother lying in a supine position (see FIG. 1). Graph 300 shows the risk to an expecting mother's fetus for the length of time that the expecting mother lies in the supine position. Graph 300 includes a risk axis 301 and a time axis 302 to show the relationship, via curve 303, between the risks of supine hypotensive syndrome and fetal hypoxia and the time that an expecting mother is lying in the supine position. It should be understood that graph 300 may not necessarily be drawn to scale and curve 303 is limited to show that the risk of fetal hypoxia increases over time as the expecting mother is lying or sleeping in the supine position.

Graph 300 features a plurality of zones 304-306. Zone 304 may represent a "neutral zone" in which the time period therein may not lead to deleterious effects on the health of the expecting mother and fetus. As such, if an expecting mother lies in the supine position for less than 5 seconds, the symptoms of supine hypotensive syndrome and fetal hypoxia may not be experienced.

Zone 305 may represent the critical time period in which an expecting mother and fetus may in some instances experience adverse health risks due to the expecting mother's supine lying position. Thus, when the expecting mother lies in the supine position for 5-7 seconds in one sitting, the fetus' health can be at risk. Zone 306 which extends from 7-9 seconds represents the time period for which lying or sleeping in the non-preferred position rapidly increases the health risk of the fetus.

Figure 4A:
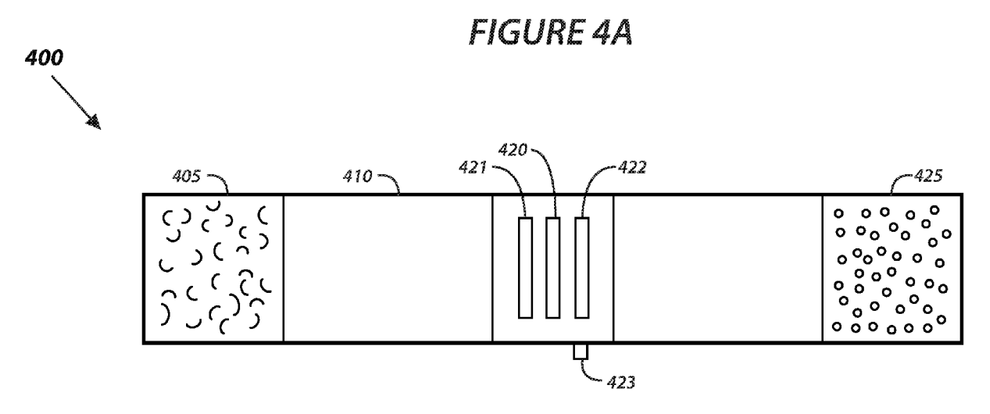
FIG. 4A is a schematic isometric view of a pregnancy belt with a set of integral sensors and alarm components.

FIG. 4A is a schematic isometric view of a pregnancy belt 400 with a set of integral sensors and alarm components. Pregnancy belt 400 comprises an adjustable belt member having an elongated axis having a first terminal end and a second terminal end. In the embodiment shown, pregnancy belt 400 comprises a substantially-axial body member 410, corresponding securing means 405, 425 (attachment), sensors 420, an alarm 421, and a power source 422. Pregnant belt 400 may also include a switch 423 coupled to the power source 422 to activate or deactivate the sensors 420 and alarm 421 components.

Securing means (attachments) 405, 425 may include a first attaching member 405 associated with a first terminal end of the pregnancy belt 400 and a second attaching member associated with a second terminal end of the pregnancy belt 400. The first attaching member and the second attaching member provides an adjustable attachment to secure around the expecting mother.

In some embodiments, sensors 420 includes a pressure sensor which is disposed substantially in the center of the belt 400 between corresponding securing means 405, 425. Sensors 420 may be configured to be worn on or near an expecting mother's back so as to detect when the expecting mother is lying in the supine position. In some embodiments, sensors 420 are configured to alert the expecting mother when she is lying in the potentially unsafe position. In addition, pregnancy belt 400 may have more than a single sensor 420 therein to detect any of various lying or sleeping positions of the expecting mother. For example, sensors 420 may be disposed substantially in the center of the pregnancy belt 400 and off to the side to confirm that the expecting mother is sleeping in the preferred left-lateral recumbent position.

Additionally, positional sensors, mercury sensors, and other sensors may be incorporated within the pregnancy belt 400. In fact, it will be apparent to those having ordinary skill in the art having the benefit of this disclosure that any sensor can be used so long as the sensor is capable of actuating or sending signals to an alarm upon detecting that the expecting mother is lying or sleeping in a supine position.

Pregnancy belt 400 may incorporate an additional sensor (or sensors) that measures the number of fetus kicks. Ordinarily, a healthy fetus receiving sufficient oxygen levels kicks 5-10 times/hr., at a minimum, whereas less than 5 kicks/hour may be an indication of oxygen deprivation. In the event that the detector number of fetus kicks falls below a threshold, one or more signals (e.g., an alert) are sent to an alarm 421.

In addition, pregnancy belt 400 may incorporate an additional sensor (or sensors) that measures the fetus' heart rate. Ordinarily, a healthy fetus has a heart rate of 120-160 beats/minute. At least one or a plurality of sensors can detect a fetus' heart rate and send an alert to alarm 421 in the event that the heart rate falls outside of a threshold range.

In preferred embodiments, pregnancy belt 400 should be comfortable when the expecting mother wears the belt 400 around her waist or torso. In addition, the pregnancy belt 400 is flexible and accommodates the expectant mother's midsection to expand as she comes to term. In some embodiments, the body member 410 comprises a soft, yet resilient material such as an elastic or similar material.

Similarly, the securing means 405, 425 are configured to be adjustable such that a single pregnancy belt 401 may be used throughout a pregnancy. In some embodiments, securing means 405, 425 comprise corresponding sides of hook and loop fasteners such as Velcro. However, it will be readily apparent to those with ordinary skill in the art having the benefit of this disclosure that a wide variety of securing means may be employed to accomplish the same or similar functionality.

As shown in FIG. 4A, set of sensors 420, an alarm, 421 and a power source 422 are integral and hard wired to the pregnancy belt 100. For example, sensors 420, alarm 421, and power source 422 are individually disposed within the pregnancy belt 400 and electrically coupled to each other with wires (not shown). Furthermore, sensors 420, alarm 421, and power source 422 may be integrated within a unitary module that fits within a pouch or sleeve formed within the pregnancy belt 400.

Figure 4B:
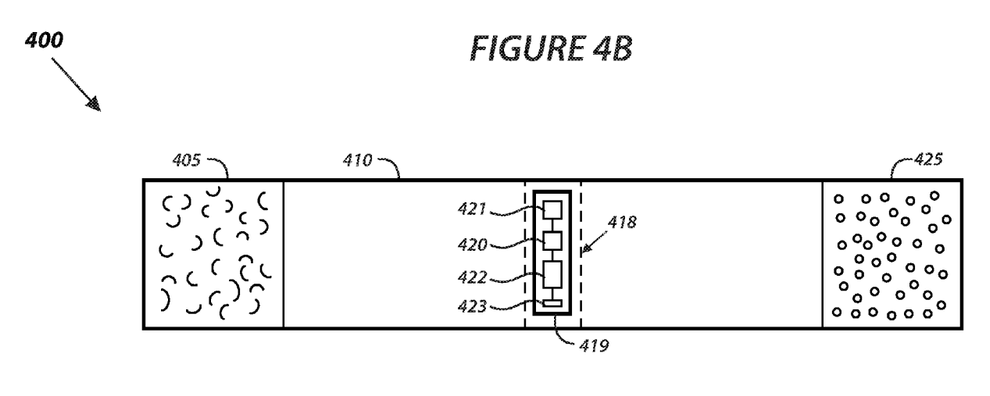
FIG. 4B is a schematic isometric view of a pregnancy belt with a unitary module therein according to the present disclosure.

FIG. 4B is a schematic isometric view of a pregnancy belt 400' with a unitary module therein. Pregnancy belt 400' comprises a substantially-axial body member 410', corresponding securing means 405', 425', and a unitary module 419'. The unitary module 419' shown comprises sensors 420', alarm 421', power source 422', and switch 423'. In some embodiments, unitary module 419' includes a pouch 418' that within the pregnancy belt 400' which includes the sensors 420', alarm 421', power source 422', and switch 423'. The unitary module 419' may be removable such that the pregnancy belt 400' may be easily laundered.

An alarm consistent with the present disclosure includes any of various notification means. For example, an alarm 421' may include one or more vibrating sub-systems which activate upon receiving one or more signals when the expecting mother is in a supine position. In some other embodiments, alarm 421' includes one or more audio sub-systems which broadcast an audio alert to notify the expecting mother of her position. For example, the alarm comprises both an auditory alarm and a vibrating apparatus. The sound level and/or vibration level is preferably adjustable based on the length of time that the expecting mother is in the supine position.

In one implementation, alai 421' alerts when sensors 420' detect that the number of fetus kicks are below a pre-defined threshold (e.g., 5 kicks/hour). Alternatively, alarm 421' engages when sensors 420' detects a fetus' heart rate is outside of a pre-defined threshold range (e.g., 120-160 heart beats/minute).

In other implementations, the alarm components are not integrated within the pregnancy belt. In this implementation, the sensors are integrally disposed in the pregnancy belt whereas the alarm is external to the belt but is in wireless communication with the sensors. Pregnancy belt 400' may further comprise a pocket (not shown) to retain a unitary module therein.

Figure 5A:
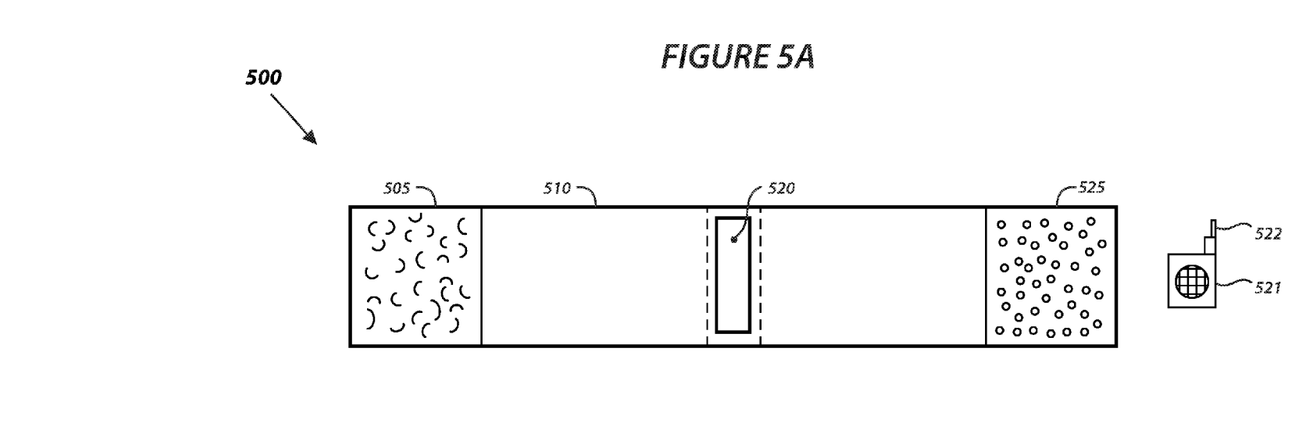
FIG. 5A is a schematic isometric view of a pregnancy belt with a set of integral sensors and external alarm.

FIG. 5A illustrates a schematic isometric view of a pregnancy belt 500 with a set of integral sensors 520 in communication with an external alarm 521. Pregnancy belt 500 comprises an adjustable belt member having an elongated axis having a first terminal end and a second terminal end. The pregnancy belt 500 further comprises securing means 505, 525. According to FIG. 5A, the sensors 520 are removably coupled to the body member 510.

Furthermore, the sensors 520 are communicatively coupled to an external alarm 521, which can be positioned at convenient locations (i.e., near an expecting mother's head and ears). In some embodiments of the present disclosure, the sensors 520 and the alarm 521 communicate using an RE signal or other wireless signal. The sensors 520 and alarm 521 communicate via an IEEE 802.11 protocol signal or a Bluetooth® signal.

According to the radio communication embodiments, the set of sensors 520 include a radio transmitter whereas the alarm 521 comprises a radio receiver 522. In use, when an expecting mother sets off the sensors 520 by lying in the supine position, the sensors 520 send one or more signals to the receiver 5 which sets off the alarm 521 to wake the expecting mother. In yet other embodiments of the present disclosure, the pregnancy belt 520 is configured to operate with sensors and an already existing alarm via a radio signal.

Figure 5B:
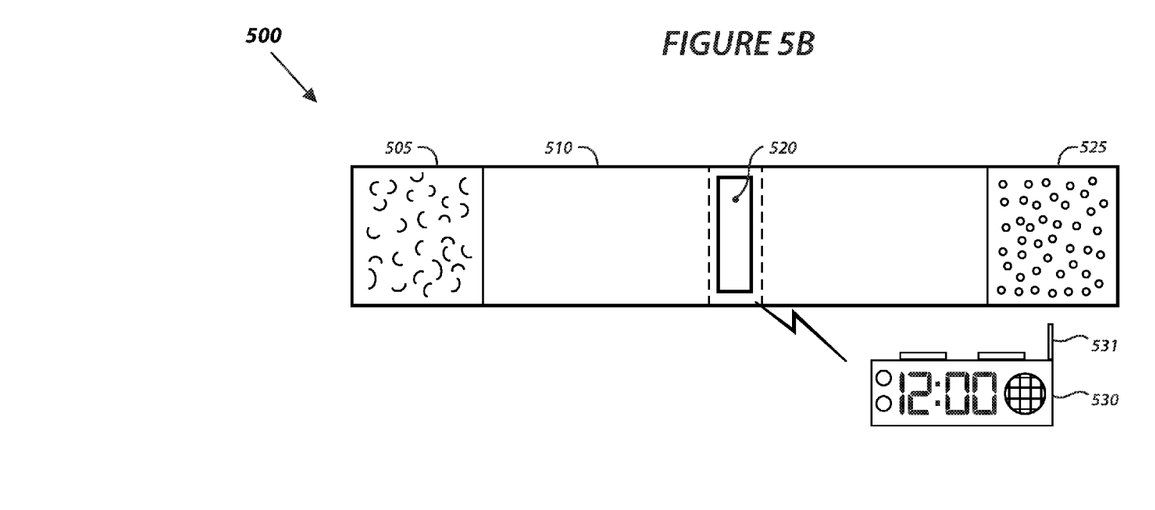
FIG. 5B is a schematic isometric view of a pregnancy belt with a set of integral sensors in radio communication with a clock radio alarm.

FIG. 5B is a schematic isometric view of a pregnancy belt 500' with a set of integral sensors in radio communication with a clock radio alarm 530. Pregnancy belt 500' comprises a substantially-axial body member 510', corresponding securing means 505', 525', and unitary module 520' which comprises sensors, a power source, and a switch. The unitary module 520' may further comprises an RF transmitter for emitting a radio frequency upon actuation of the sensors. In some embodiments, the frequency of the signals is constant. In some other embodiments, the frequency of the signal is adjustable.

The clock radio 530 includes an antenna 531 for receiving radio signals. The clock radio 530 is set to broadcast an alarm upon sensing the operating frequency emitted from the pregnancy belt 500.

In operation, the unitary module 520' emits a unique radio frequency when actuated by an expecting mother lying on the sensors. Accordingly, the clock radio 530 may broadcast an alarm upon sensing the unique radio frequency thus alerting the expecting mother.

The circulatory system of the expecting mother and fetus allows the best oxygenation and blood flow when the expecting mother lies on her left side. Therefore, in some other embodiments of the present disclosure, a pregnancy belt is configured to alert, in a non-intrusive manner (e.g., soft tones) when an expecting mother is sleeping on her left side.

Figure 6:
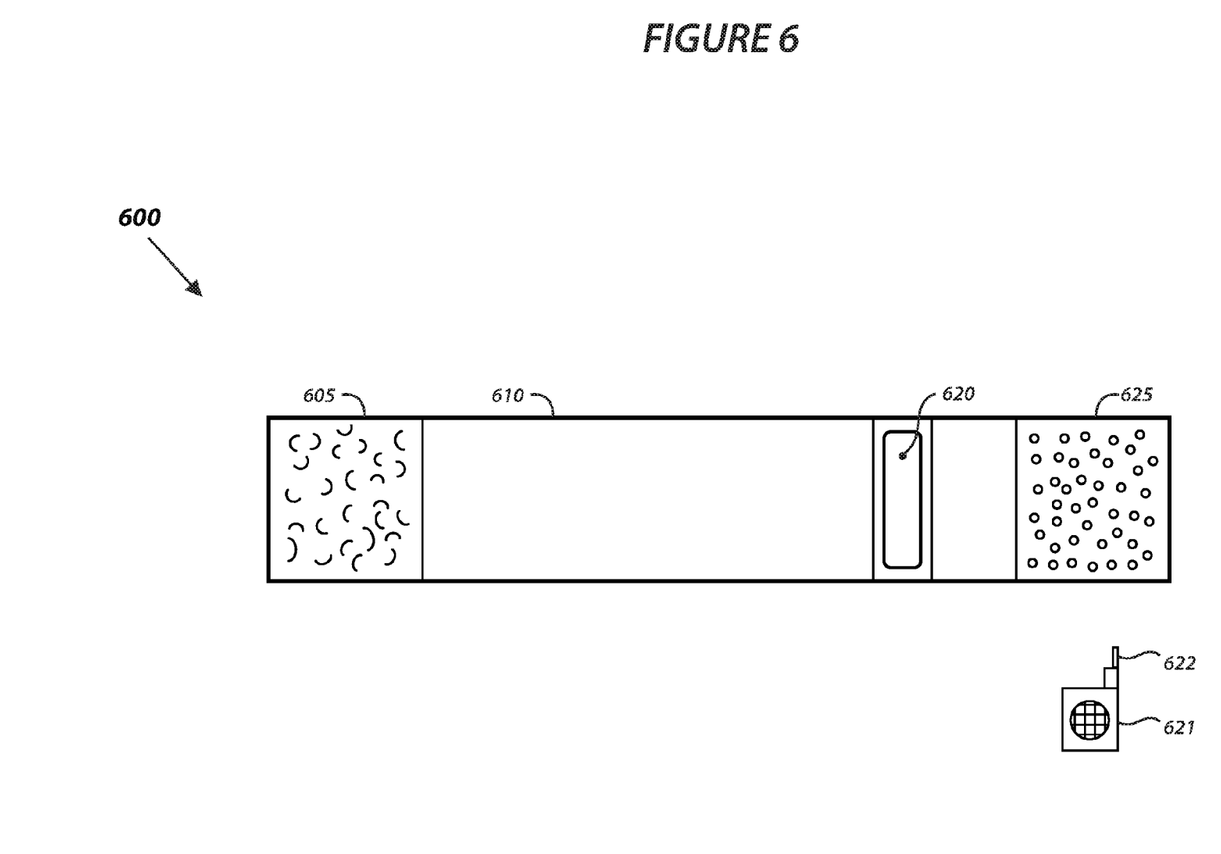
FIG. 6 is a schematic isometric view of a pregnancy belt with sensors that is disposed off-center on the pregnancy belt.

FIG. 6 illustrates a schematic isometric view of a pregnancy belt 600 with sensors that is disposed off-center on the pregnancy belt. Pregnancy belt 600 comprises an adjustable belt member having an elongated axis having a first terminal end and a second terminal end. Wireless alarm 621 comprises a receiver 622 and corresponding securing means 605, 625. As shown, the sensors 620 are disposed off-center on the pregnancy belt 600 such that it is positioned under an expecting mother's side while lying or sleeping. In the embodiment, the sensors 620 is disposed on the pregnancy belt 600 such that it is positioned under the expecting mother's left side while lying or sleeping. As such, the sensors 620 may detect when the expecting mother is not lying on the preferred side of her body while wearing the pregnancy belt 600.

Figure 7:
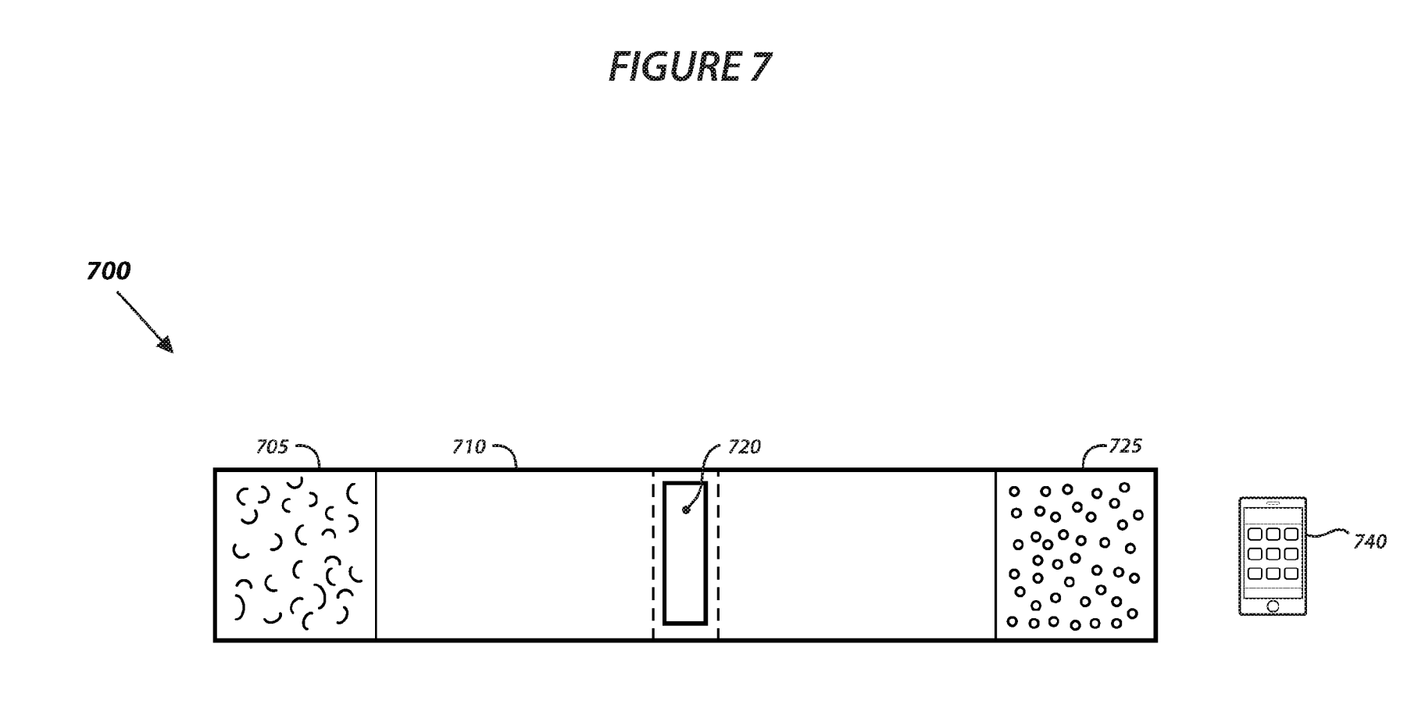
FIG. 7 is a schematic isometric view of a pregnancy belt in communication with an external smartphone device.

FIG. 7 is a schematic isometric view of a pregnancy belt 700 in communication with an external smartphone device 740. Pregnancy belt 700 comprises an adjustable belt member having an elongated axis having a first terminal end and a second terminal end. The pregnancy belt 700 comprises a substantially-axial body member 710, sensors 720, and corresponding securing means 705, 725. Smartphone device 740 may comprise a software application installed on the device 740 which is operable to activate an alarm function. In some implementations, smartphone device 740 includes a software application which features an alarm component that is activated based on a signal received from the pregnancy belt 700. Smartphone device 740 may be communicatively coupled with the sensors 720 of the pregnancy belt 700 via a wireless network.

Figure 8:
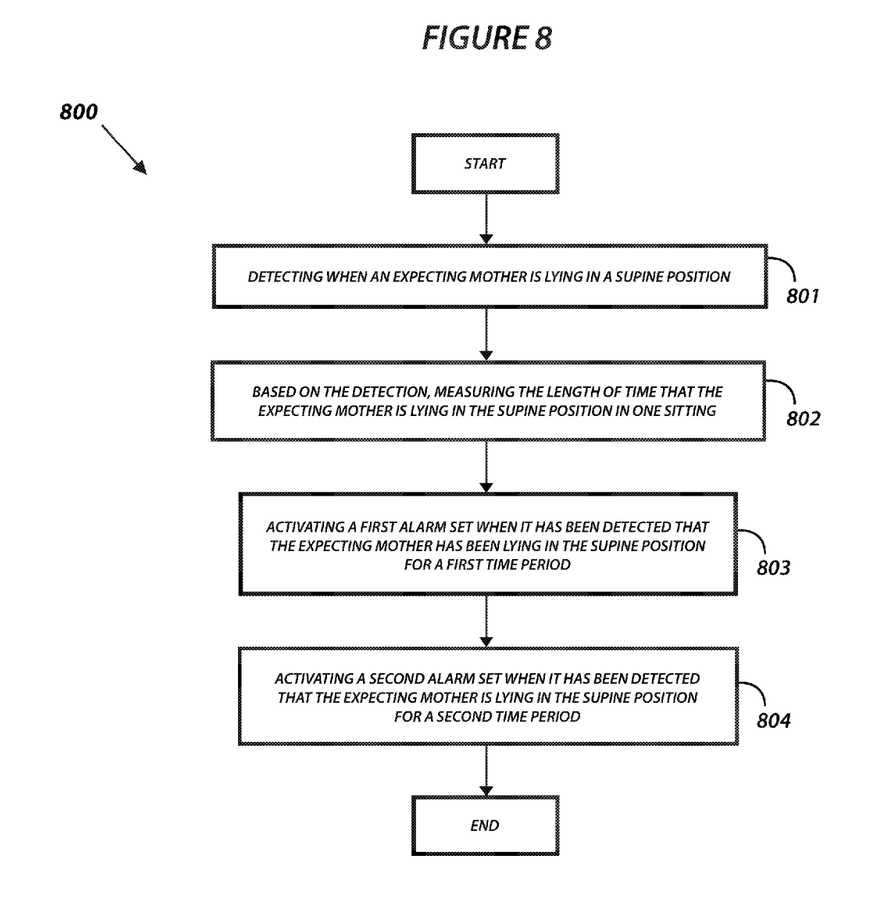
FIG. 8 is a flowchart of a method consistent with the present disclosure.

FIG. 8 is a flowchart 800 of a method consistent with the present disclosure. Flowchart 800 begins with block 801—detecting when an expecting mother is lying in a supine position. Next, based on the detection, measuring the length of time that the expecting mother is lying in the supine position in one sitting (block 802).

Further, activating a first alarm set when it has been detected that the expecting mother has been lying in the supine position for a first time period (block 803). In some implementations at least one alarm within the first alarm set and at least one alarm within the second alarm set are different. The first alarm set and the second alarm set may include at least one auditory alarm and vibration apparatus. In some embodiments, the first alarm set includes an alarm which emanates from an alarm component disposed on an alarm belt wherein the second alarm set includes an alarm which emanates from an alarm component of a device external to the alarm belt.

Next, activating a second alarm set when it has been detected that the expecting mother is lying in the supine position for a second time period (block 804). In some embodiments, the first time period is in the range of 5 to 7 seconds and the second time period exceeds 7 seconds. Lastly, flowchart 800 may include deactivating the first and second alarm sets upon detecting that the expecting mother is no longer lying in the supine position.

In some other embodiments of the present disclosure, the position of the set of sensors is adjustable and may toggle between alerting the expecting mother when she is lying on it and alerting the expecting mother when she is not lying on it. According to these embodiments, the belt and sensors are able to either alert an expecting mother when she is lying in the supine position and/or notify her when she is not sleeping on her left side.

In addition, a method consistent with the present disclosure may be further adapted to detect when a number of kicks by a fetus is below a first pre-defined threshold and when the heart rate is not within a second pre-defined threshold.

As will be understood by those familiar with the art, the present disclosure may be embodied in other specific forms without departing from the spirit or essential characteristics thereof. Likewise, the particular naming and division of the members, features, attributes, and other aspects are not mandatory or significant, and the mechanisms that implement the present disclosure or its features may have different names, divisions and/or formats. Accordingly, the disclosure of the present disclosure is intended to be illustrative, but not limiting, of the scope of the present disclosure, which is set forth in the following Claims.

Reference throughout this specification to "one embodiment" or "an embodiment" means that a particular feature, structure, or characteristic described in connection with the embodiment is included in at least one embodiment of the present disclosure. Thus, the appearances of the phrases "in one embodiment" or "in some embodiments" in various places throughout this specification are not necessarily all referring to the same embodiment. Furthermore, the particular features, structures, or characteristics may be combined in any suitable manner in one or more embodiments.

In the foregoing specification, a detailed description has been given with reference to specific exemplary embodiments. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense. Furthermore, the foregoing use of embodiment and other exemplarily language does not necessarily refer to the same embodiment or the same example, but may refer to different and distinct embodiments, as well as potentially the same embodiment.

What is claimed is:

1. A wearable apparatus, comprising:
   an adjustable belt member having an elongated axis of sufficient length to cover the girth of an expecting mother during an entire term of her pregnancy;
   the adjustable belt member having an alarm component coupled thereto;
   an attachment coupled to the adjustable belt member to secure the adjustable belt member to the expecting mother;
   a set of sensors to detect when the expecting mother is lying in a supine position, a number of fetal kicks, and a heart rate of a fetus;
   wherein the set of sensors are to send at least one signal to the alarm component;
   based on the detection,
      measuring a length of time that the expecting mother is lying in the supine position;
      activating a first alarm when the expecting mother is lying in the supine position for a first time period to indicate to the expecting mother that she is lying correctly in the supine position;
      measuring the number of fetal kicks for a second time period and the heart rate of the fetus for a third time period;
      activating a second alarm when the number of fetal kicks is outside of a first predetermined range for the second time period;
      activating a third alarm when the number of fetal kicks is outside of the first predetermined range for a third time period;
      wherein the third time period is greater and extends later in time than the second time period;
      activating the second alarm when the heart rate of the fetus is outside of a second predetermined range for a fourth time period; and
      activating the third alarm when the heart rate of the fetus is outside of the second predetermined range for a fifth time period;
      wherein the fifth time period is greater and extends later in time than the fourth time period;
   a power source coupled to the set of sensors to provide power thereto.

2. The wearable apparatus of claim 1 wherein the alarm component is coupled to the set of sensors to alert the expecting mother when the expecting mother is lying in the supine position.

3. The wearable apparatus of claim 2, wherein the set of sensors are to further detect when a number of kicks by a fetus is below a first pre-defined threshold, or when the heart rate is not within a second pre-defined threshold.

4. The wearable apparatus of claim 3, wherein the first pre-defined threshold is five fetus kicks per hour and the second pre-defined threshold is between 120 and 160 feTus heartbeats per minute.

5. The wearable apparatus of claim 1, wherein the attachment comprises:
   a first attaching means;
   a second attaching means,
   wherein the first attaching means is substantially disposed on a first terminal end of the adjustable belt member and the second attaching means is substantially disposed on a second terminal end of the adjustable belt member; and wherein the first and second attaching means are removably joinable to the other.

6. The wearable apparatus of claim 4, the first attaching means comprising a portion of fabric containing hook members of a hook and loop fastener, and the second attaching means comprising a portion of fabric containing loop members of a hook and loop fastener.

7. The wearable apparatus of claim 1, further comprising a switch coupled to the power source for activating and deactivating the sensor.

8. The wearable apparatus of claim 2, wherein the set of sensors, the alarm component, and the power source are integrated within a unitary module, and wherein the unitary module is removably coupled to the adjustable belt member.

9. The wearable apparatus of claim 2, wherein the set of sensors are disposed within the belt, and wherein the alarm component is remotely located and in wireless communication with the set of sensors.

10. The wearable apparatus of claim 9, the sensor further comprising:
    a transmitter for sending data wirelessly to the alarm;
    the alarm further comprising a receiver capable of receiving wireless data from the set of sensors for converting the wireless data into an alarm signal when the expecting mother is lying upon the set of sensors.

11. The wearable apparatus of claim 1, wherein the alarm component comprises an auditory alarm.

12. The wearable apparatus of claim 1, wherein the alarm component comprises a vibration apparatus.

13. A method, comprising:
    employing an adjustable belt member to detect a lying position of an expecting mother, a number of fetal kicks, and a heartrate of a fetus;
    based on the detection,
       measuring the length of time that the expecting mother is lying in a supine position;

activating a first alarm when the expecting mother is lying in the supine position for a first time period to indicate to the expecting mother that she is lying correctly in the supine position;

measuring the number of fetal kicks for a second time period and the heart rate of the fetus for a third time period;

activating a second alarm when the number of fetal kicks is outside of a first predetermined range for the second time period;

activating a third alarm when the number of fetal kicks is outside of the first predetermined range for a third time period;

wherein the third time period is greater and extends later in time than the second time period;

activating the second alarm when the heart rate of the fetus is outside of a second predetermined range for a fourth time period; and activating the third alarm when the heart rate of the fetus is outside of the second predetermined range for a fifth time period;

wherein the fifth time period is greater and extends later in time than the third time period and the third alarm and the fifth alarm are different.

14. The method of claim 13, wherein the first alarm and the second alarm are different.

15. The method of claim 13, wherein the first alarm is disposed on an adjustable belt member and the second alarm is a component of a device external to the adjustable belt member.

16. The method of claim 13, wherein a first sensor of the set of sensors of an adjustable belt member can detect when an expecting mother is lying in the supine position, a second sensor of the set of sensors detect when a number of kicks by a fetus is below a first pre-defined threshold, and a third sensor of the set of sensors detect when a heart rate of the fetus is not within a second pre-defined threshold.

17. The method of claim 13, wherein the first time period is in the range of 5 to 7 seconds and the second time period exceeds 7 seconds.

18. A pregnancy belt system, comprising:

an adjustable belt member having an elongated axis having a first terminal end and a second terminal end, the adjustable belt member comprising a soft and resilient material;

an attachment for securing the adjustable belt member to an expecting mother, the attachment comprising a first attaching member associated with the first terminal end of the adjustable belt member and a second attaching member associated with the second terminal end of the adjustable belt member, the first attaching member and the second attaching member providing an adjustable attachment of the adjustable belt member around the expecting mother;

a set of sensors to detect when the expecting mother is lying in the supine position, a number of fetal kicks and a heart rate of the fetus; and based on the detection, measuring a length of time that the expecting mother is lying in the supine position;

activating a first alarm when the expecting mother is lying in the supine position for a first time period to indicate to the expecting mother that she is lying correctly in the supine position;

measuring the number of fetal kicks for a second time period and the heart rate of the fetus for a third time period;

activating a second alarm when the number of fetal kicks is outside of a first predetermined range for the second time period;

activating a third alarm when the number of fetal kicks is outside of the first predetermined range for a third time period;

wherein the third time period is greater and extends later in time than the second time period;

activating the second alarm when the heart rate of the fetus is outside of a second predetermined range for a fourth time period; and activating the third alarm when the heart rate of the fetus is outside of the second predetermined range for a fifth time period;

wherein the fifth time period is greater and extends later in time than the fourth time period;

a smartphone device that is equipped with an alarm function, operable to execute the first, second, third, and fourth alarms, that is external to the adjustable belt member and to be communicatively coupled with the adjustable belt member.

19. The pregnancy belt system of claim 18, wherein the smartphone device contains an alarm function.

20. The pregnancy belt system of claim 18, wherein the smartphone device is to be communicatively coupled with the pregnancy belt via a wireless network.

\* \* \* \* \*